United States Patent [19]
Kitchell et al.

[11] Patent Number: 5,403,595
[45] Date of Patent: Apr. 4, 1995

[54] CONTROLLED, SUSTAINED RELEASE DELIVERY SYSTEM FOR SMOKING CESSATION

[75] Inventors: Judith P. Kitchell, Newton; Indu A. Muni, N. Reading; Yvonne N. Boyer, Salem, all of Mass.

[73] Assignee: DynaGen, Inc., Cambridge, Mass.

[21] Appl. No.: 135,847

[22] Filed: Oct. 13, 1993

Related U.S. Application Data

[63] Continuation of Ser. No. 881,740, May 7, 1992, abandoned, which is a continuation-in-part of Ser. No. 696,637, May 7, 1991, abandoned.

[51] Int. Cl.⁶ .................. A61K 9/50; A61K 9/70; A61K 9/48

[52] U.S. Cl. .................. 424/501; 424/423; 424/425; 424/426; 424/449; 424/451; 424/489; 424/502; 514/810; 514/811; 514/812; 514/813; 514/963; 514/965

[58] Field of Search ............ 424/422, 423, 425, 426, 424/449, 486, 489, 501, 502, 451; 514/810, 811, 812, 813, 963, 965; 428/402

[56] References Cited

U.S. PATENT DOCUMENTS

| | | | |
|---|---|---|---|
| 3,862,946 | 1/1975 | Havera | 260/293 |
| 3,879,555 | 4/1975 | Pachter et al. | 424/260 |
| 3,885,027 | 5/1975 | Shaw et al. | 424/44 |
| 3,887,699 | 6/1975 | Yolles | 424/19 |
| 3,906,100 | 9/1975 | Havera | 424/267 |
| 3,947,592 | 3/1976 | Grosz | 424/330 |
| 3,966,940 | 6/1976 | Pachter | 424/260 |
| 3,976,071 | 8/1976 | Sadek | 128/260 |
| 3,980,766 | 9/1976 | Shaw et al. | 424/10 |
| 4,144,228 | 3/1979 | Jones et al. | 260/112.5 |
| 4,145,435 | 3/1979 | Szmuszkovicz | 424/274 |
| 4,177,056 | 12/1979 | Mueller | 71/93 |
| 4,192,827 | 3/1980 | Mueller | 525/123 |
| 4,248,855 | 2/1981 | Blank et al. | 424/19 |
| 4,277,582 | 7/1981 | Mueller et al. | 525/421 |
| 4,304,591 | 12/1981 | Mueller et al. | 71/93 |
| 4,344,431 | 8/1982 | Yolles | 128/260 |
| 4,361,553 | 11/1982 | Loh et al. | 424/177 |
| 4,380,550 | 4/1983 | Kleinlogel et al. | 424/324 |
| 4,444,758 | 4/1984 | Scherschlicht et al. | 424/177 |

(List continued on next page.)

FOREIGN PATENT DOCUMENTS

| | | |
|---|---|---|
| 914065 | 11/1972 | Canada . |
| 1273878 | 9/1990 | Canada . |
| 0272918 | 6/1988 | European Pat. Off. . |
| 280413 | 8/1988 | European Pat. Off. . |
| 1-197435 | 1/1988 | Japan . |
| 389829 | 3/1965 | Switzerland . |

OTHER PUBLICATIONS

Dorsey, J., "Control of the Tobacco Habit", Ann. Int. Medicine 10: 628–631 (1936).

Hoffstaedt, E., "The Use of Lobeline in the Treatment of Smokers" The Medical Journal of Australia (Feb. 24, 1964).

Kalyuzhnyy, V. V., [English Translation of Russian Original], J. of Neural Psychiat. 68: 1864–1870 (1968).

London, S. J., "Clinical Evaluation of a New Lobeline Smoking Deterrent", Current Therapeutic Res. 5: 167–175 (1963).

Perlstein, I. B., Symposium on Recent Advances in the
(List continued on next page.)

Primary Examiner—Thurman K. Page
Assistant Examiner—Carlos Azpuru
Attorney, Agent, or Firm—Wolf, Greenfield & Sacks

[57] ABSTRACT

A drug delivery system useful in aiding individuals in the cessation of smoking or chewing nicotine containing products is described. The delivery system includes a physical constraint modulation system (PCMS ™) containing lobeline. The drug delivery system is capable of delivering lobeline to an individual in a controlled, sustained release manner and providing long-term therapeutic levels of lobeline to the individual. The delivery of lobeline in such a manner reduces or eliminates the individual's smoking or chewing habit. The PCMS may be a biodegradable polymer containing the lobeline capable of subcutaneous or intramuscular injection or implantation into the individual or may be part of a transdermal patch containing lobeline. Also described are methods of using the drug delivery systems and kits containing the drug delivery systems.

10 Claims, 9 Drawing Sheets

U.S. PATENT DOCUMENTS

| | | | |
|---|---|---|---|
| 4,464,378 | 8/1984 | Hussain | 424/260 |
| 4,592,753 | 6/1986 | Panoz | 604/897 |
| 4,620,977 | 11/1986 | Strahilevitz | 424/88 |
| 4,624,665 | 11/1986 | Nuwayser | 604/307 |
| 4,632,935 | 12/1986 | Kaplan | 514/429 |
| 4,698,342 | 10/1987 | Crosby | 514/253 |
| 4,719,215 | 1/1988 | Goldberg | 514/282 |
| 4,745,160 | 5/1988 | Churchill et al. | 525/415 |
| 4,749,576 | 6/1988 | Lee | 424/486 |
| 4,767,628 | 8/1988 | Hutchinson | 424/426 |
| 4,789,726 | 12/1988 | Hutchinson | 528/354 |
| 4,822,617 | 4/1989 | Panoz | 424/449 |
| 4,834,973 | 5/1989 | Strahilevitz | 424/85.8 |
| 4,873,086 | 10/1989 | Good et al. | 424/409 |
| 4,898,734 | 2/1990 | Mathiowitz et al. | 424/426 |
| 4,908,213 | 3/1990 | Govil et al. | 424/447 |
| 4,920,989 | 5/1990 | Rose et al. | 131/270 |
| 4,927,676 | 4/1990 | Heiber et al. | 424/449 |
| 4,935,428 | 6/1990 | Lewis | 514/282 |
| 4,943,435 | 7/1990 | Baker et al. | 424/486 |
| 4,956,391 | 9/1990 | Sapse | 514/810 |
| 4,963,367 | 10/1990 | Ecanow | 424/485 |
| 4,994,260 | 2/1991 | Kallstrand et al. | 424/10 |
| 4,996,047 | 2/1991 | Kelleher et al. | 424/79 |
| 5,030,216 | 7/1991 | Theeuwes et al. | 604/892 |
| 5,055,478 | 10/1991 | Cooper et al. | 424/48 |

OTHER PUBLICATIONS

Mecical Aspects of Smoking, The Matthew Publish. Co., N.Y. 40–45 (1964).

Prignot, J., "Pharmacological Approach to Smoking Cessation", Eur. Respir. J. 2: 550–560 (1969).

Swartz, H., "Clinical Evaluation of SMOKURB...", Current Therapeutic Research 6: 290–296 (1964).

Scott, G. W. et al., "Buffered Lobeline as a Smoking Deterrrent", Lancet, 58–59, Jan. 6, 1962.

Davison, G. et al., "Lobeline and Reduction of Cigarette Smoking" Psychological Reports 31: 443–446 (1972).

Merry, J. et al., "The Effect of Buffered Lobeline...", Practitioner 190: 628–631 (1963).

Rapp, G. W. et al., "A Critical Evaluation of a Lobeline Based Smoking Deterrent", Amer. J. Med. Sci. 230: 9–14 (1955).

Rapp, G. W. et al., "Absorption and Utility of Lobeline As A Smoking Deterrent", Amer. J. Med. Sci. 237: 287–292 (1959).

Wright, I. et al., "Lobeline Sulfate: Its Pharmacology and Use..." J. Amer. Med. Assn.: 109, 649–654 (1937).

Schuster, C. R. et al., Chapter 8: "The Effects of d-Amphetamine, Meprobate, and Lobeline on the Cigarette Smoking Behavior" (1979).

Mullenix, P. et al., "The Effects of Nicotine and Lobeline on Spontaneous Behavior of Adult Male Rats", (Forsyth Research Institute, Boston, Mass., sponsored by DynaGen, Inc., Cambridge, Mass. (1990).

Reavill, C., et al., "High Affinity Binding of [3H] (−)-Nicotine to Rat Brain Membranes...", Neuropharmacology 27: 235–241 (1988).

Sloan, J. W., et al., "The Comparative Binding Characteristics of Nicotinic Ligands...", Pharmacol. Biochem. Behav. 30(1): 255–267 (1988).

Takagi et al., "Lobeline-containing Skin Patch to discourage tobacco smoking", 63–6 Pharmaceuticals, 1989 (Abstract).

Derwent File Supplier WPI(L), AN=89-273364 [38], Derwent Publications Ltd, London, GB, & JPA,1197435 (Teikoku Seiyaku K.K.) Sep. 9, 1989.

Deasy, P. B., "Microencapuslation and related druf processes," Marcel Dekker, Inc., New York, pp. 223–224, Chapter 10.1.2: Narcotic antagonists (1984).

CONTROLLED, SUSTAINED RELEASE DELIVERY SYSTEM FOR SMOKING CESSATION

RELATED APPLICATION

This application is a continuation of application Ser. No. 07/881,740, filed May 7, 1992, now abandoned, which is a continuation-in-part of related application Ser. No. 07/696,637, filed May 7, 1991, now abandoned, for A CONTROLLED, SUSTAINED RELEASE DELIVERY SYSTEM FOR SMOKING CESSATION.

FIELD OF THE INVENTION

Embodiments of the present invention feature drug delivery systems which deliver a controlled, sustained release of lobeline for the treatment of nicotine dependency.

BACKGROUND

Recent studies have linked smoking to both heart disease and cancer. Smoking also may adversely affect a fetus during pregnancy. A trend thus has developed towards people wanting to quit smoking. It is difficult for a person to quit smoking since nicotine, a component of tobacco, is an addictive drug ("Nicotine Addiction", a report of the Surgeon General, 1988). Presently available over-the-counter products for aiding in smoking cessation are not always successful.

Lobeline is an alkaloid obtained from the dried leaves and tops of the Indian tobacco herb, *Lobella inflata*. Lobeline is a substituted piperidine compound that produces several physiological affects, some of which are similar to those produced by nicotine. Lobeline's potency in causing these physiological effects is significantly less than that of nicotine. Because of lobeline's pharmacological similarities with nicotine, it has been considered as a substitute for nicotine which assists individuals in lessening addiction to nicotine and in ceasing to smoke cigarettes. Although use of lobeline as a smoking cessation aid has been studied since at least the 1930's, its efficacy has been a matter of dispute. Moreover, severe, undesirable side-effects have been reported.

Presently available over-the-counter products (Nikoban ®, Bantron ®, CigArrest ™, and Nic-Fit) offer lobeline hemi-sulfate as an aid to smoking cessation. These products are taken orally and the recommended daily doses are up to 6 milligrams. Antacids are incorporated in some of the products to overcome gastrointestinal discomfort, a side effect similar to that caused by nicotine. Higher oral doses may not be feasible because of the concomitant gastric upset. The efficacy of oral doses of lobeline at 6 mg/per day in aiding smoking cessation has not been proven.

The presently available over-the-counter lobeline formulations for treating smoking addiction either do not appear to provide or do not appear to maintain therapeutic blood or tissue levels of lobeline. This may be because of the low dose of lobeline in the lobeline formulations, poor absorption of oral formulations or metabolism which does not allow lobeline to reach critical therapeutic levels.

Although there have been reports of using lobeline in oral formulations at doses in excess of 10 mg/day, nausea and even vomiting have been associated with such doses. A further problem with such oral dose regimens is that self-administration of as many as 18 tablets per day has been required. This not only may be considered by patients as intrusive, but also does not permit the physician to carefully control dosage.

Kalyuzhnyy (*J. of Neural Psychiat* 68: 1864–1870 (1968)) describes the use of intramuscular doses of lobeline hemi-sulfate up to 10 mg/per injection, administered twice daily. Although the amount of lobeline administered by Kalyuzhnyy was reported to be effective, the procedure for administration does not lend itself to practical application because it requires twice daily injections of lobeline.

Takagi et al. (JP 1-197,435) describe a smoking-substitute adhesive agent containing 0.5 to 10 percent lobeline by weight. Takagi et al. report that blood concentrations of lobeline remained higher for several hours compared to blood concentrations of nicotine delivered using the same adhesive agent delivery system. Takagi et al. did not report the amounts of lobeline released from the adhesive agent.

SUMMARY OF THE INVENTION

The present invention provides a drug delivery system useful in aiding individuals in the cessation of smoking or chewing nicotine containing products by providing a delivery system for releasing a controlled amount of lobeline. The delivery system eliminates the need for twice daily injections or multiple daily doses of lobeline, and is capable of providing lobeline at therapeutically effective levels for long periods of time.

The drug delivery system has a physical constraint modulation system (hereinafter PCMS) containing lobeline. It is constructed and arranged so that lobeline is delivered to the individual at therapeutic levels in a controlled, sustained release manner. The delivery of lobeline in such a manner reduces or eliminates the individual's desire to smoke or chew nicotine containing products.

The PCMS may involve a biodegradable polymer suitable for subcutaneous or intramuscular injection into the individual or may be part of a transdermal patch applied to the skin of an individual. In the PCMS utilizing the biodegradable polymer, the form of the delivery system preferably is microparticles which are suspended in a pharmaceutically acceptable vehicle just prior to subcutaneous or intramuscular injection.

The PCMS utilizing the transdermal patch may employ, for example, a diffusion layer matrix containing lobeline, or may be a multicompartmental patch containing the lobeline in a first compartment and a delivery substance in a second compartment. The lobeline, is released from the first compartment when contacted with the delivery substance. The transdermal patch having the diffusion layer typically is replaced every seven days and, the multicompartmental transdermal patch typically is replaced on a daily basis.

The present invention also pertains to a method for treating an individual for nicotine dependence, i.e., cessation of smoking or chewing nicotine containing products. The method includes administering lobeline, to the individual in a controlled, sustained release manner such that long-term therapeutic levels of lobeline are provided to the individual. This method preferably is carried out using the delivery systems described above. The lobeline may be administered to the individual at time periods easily integrated with behavioral modification support programs.

The present invention also pertains to kits useful in treating nicotine dependence. For example, the kits are useful in aiding individuals in the cessation of smoking or chewing nicotine containing products. The kits contain a sustained release system of the type herein described capable of delivering long-term therapeutic levels of lobeline, along with instructions providing information to the user and/or health care provider regarding the use of the system for aiding in the cessation of smoking or chewing a nicotine containing product. The preferred kits include a delivery system capable of providing sustained release of therapeutic levels of lobeline for at least three weeks.

It is an object of the invention to provide a controlled, sustained release delivery system for passively providing long-term therapeutic levels of lobeline to individuals.

It is another object of the invention to provide a delivery system capable of delivering lobeline to an individual in a manner which reduces or eliminates the individual's tobacco smoking or chewing habit.

It is yet another object of the invention to provide a drug delivery system for delivering lobeline to an individual without passage of the drug through the gastrointestinal (GI) tract thereby minimizing GI side effects.

It is yet a further object of the invention to provide a drug delivery system for delivering lobeline, in doses which are not overly intrusive to the individual and are easily integrated with a behavioral modification program designed to help the individual quit smoking.

It is yet another object of the invention to provide self-administratable, drug delivery systems for delivering lobeline, in therapeutically effective amounts.

Still another object of the invention is to provide therapeutic levels of lobeline, without the need for multiple, daily doses.

DETAILED DESCRIPTION

The present invention pertains to a method for treating an individual for nicotine dependence. The method comprises administering a therapeutic level of lobeline to the individual in a controlled, sustained release manner over a period of time having a duration of at least one day. The method is particularly useful in combination with a smoking cessation program. Such programs combine therapies for treating an individual's physical dependence on nicotine with behavior modification counseling directed to reducing the individual's psychological addiction to smoking or chewing nicotine-containing products.

The preferred methods of the invention involve administration regimens that are easily integrated with smoking cessation behavioral modification programs. These programs are designed to teach individuals how to quit or reduce their use of nicotine-containing products, by modifying their behavior. Typically, these programs involve regularly scheduled, e.g. weekly or biweekly, meetings with counselors.

The language "time periods easily integrated with smoking cessation behavioral modification support programs" is intended to include time periods which coincide with regularly scheduled meetings with counselors, e.g. weekly or biweekly. For example, the delivery system may be designed such that weekly subcutaneous or intramuscular injections are required to maintain a therapeutic level of lobeline in the individual's circulatory system. The weekly injections are easily coordinated with a weekly appointment with a counselor from a behavioral modification support program. Preferably, the injection is administered by medical personnel or the counselor. The individual may schedule a weekly appointment for obtaining both the injection and any necessary behavioral support counseling.

The present invention also pertains to a drug delivery system useful in aiding an individual in the cessation of smoking or chewing nicotine containing products. The delivery system includes a physical constraint modulation system (PCMS) containing lobeline. The system is constructed and arranged to deliver a therapeutic level of lobeline to the individual in a controlled, sustained release manner for a period of time having a duration of at least one day. Typically, the delivery system is constructed and arranged such that the physical constraint modulation system subcutaneously, intramuscularly or transdermally delivers lobeline into the circulatory system.

The drug delivery system is used to provide long-term therapeutic levels of lobeline, to the individual. Delivering the lobeline in such a manner reduces or eliminates the individual's smoking or chewing habit.

The term individual refers broadly to individuals who suffer from nicotine dependency. Thus, individuals refers to individuals who smoke or chew nicotine containing products. The nicotine containing products may be any product containing nicotine, e.g. cigarettes, pipe tobacco, and chewing tobacco.

The term PCMS is intended to include substances or components, e.g. solids, liquids, gels or layers, capable of releasing lobeline, in a sustained release manner. Examples of PCMS which are useful within the present invention include biodegradable polymers and parts of transdermal patches.

The term lobeline is intended to include 2-[6-(B-hydroxyphenethyl)-1-methyl-2-piperidyl] acetophenone as shown below. The lobeline may be in its free base form or may be in the form of a water soluble salt, e.g. hydrochloride or sulfate salts, or a less soluble salt, e.g. palmoate.

where X is the anion.

The term lobeline also is intended to encompass structural equivalents of the above compound which share the same or similar functional characteristics. Structural equivalents are structurally similar to the above compound but may have one or more substituents on the core structure. For example, substituents may be placed on either of the benzene rings as long as the substituents do not adversely affect the compound's ability to act as a substitute for nicotine. Examples of substituents may include lower alkyl groups, e.g. methyl, ethyl and propyl groups. For a further example, the methyl group of the piperidyl nitrogen may be substituted with a different lower alkyl group, e.g. ethyl or propyl group.

The term "controlled, sustained release manner" is intended to include the delivery of lobeline, in a manner in which only a portion of the lobeline is released from the PCMS at a given moment while the remaining lobeline is retained in the PCMS and released gradually over an extended period of time. The extended period of time is a period of time having a duration of at least a day (twenty-four hours), but may be longer such as up to about thirty days or even ninety days.

The long-term therapeutic levels of lobeline are intended to include those levels of lobeline sufficient to significantly reduce or eliminate the individual's habit for smoking or chewing a nicotine containing product over an extended period of time, as defined above. Examples of such therapeutic levels include from about five to about thirty milligrams of lobeline per day, preferably averaging between about ten to about twenty milligrams per day over time periods of about one to at least about thirty days. These doses are based on the free base form of lobeline. This dose of about five to about thirty mg of lobeline is the amount of lobeline released from the PCMS and does not refer to the level of lobeline detected in the individual's circulatory system.

The PCMS of the drug delivery system may be in a form suitable for subcutaneous or intramuscular injection, such as combined with a biodegradable polymer. The term biodegradable polymer includes polymers capable of degrading in vivo and delivering the lobeline, in a controlled, sustained release manner such that long-term therapeutic levels of lobeline are attainable.

The polymer is selected such that it does not cause significant adverse effects to the individual when administered in vivo. Examples of biodegradable polymers which may be used in this invention include poly(-lactic/glycolic)acid copolymers (PLGA), polylactic acid (PLA), polyglycolic acid (PGA), polyesters, e.g. polyorthoesters, polylactones, polyanhydrides, and polyaminoacids. The preferred biodegradable polymer is PLGA.

Polymers prepared from glycolide and lactide dimers e.g., PLGA, PLA and PGA, are known to undergo slow hydrolysis when implanted in tissue and the byproducts of their hydrolysis (lactic and glycolic acids) both are normal metabolites. PLOA, PLA, and PGA are believed to be non-toxic, are relatively non-inflammatory, and non-tissue reactive. The polymers also exhibit moderate strength and tension, compression and pliability. Hereinafter, the term PLGAs will be used to encompass PLA, PGA, and PLGA.

The specific lactide/glycolide ratio of the PLGAs polymer and the molecular weight of the polymer are factors considered when designing the drug delivery system. There are differences in the hydrophobicity and crystallinity of lactic acid, and glycolic acid, and the use of a fast-hydrolyzing polymer (low molecular weight, low lactide content) for rapid ultimate clearance of lobeline, is balanced with the need for the sustained release of relatively soluble lobeline provided by a slow-hydrolyzing polymer (high molecular weight, high lactide content). Based on these needs, the preferred polymers for delivery of lobeline are in the range of about 50:50 lactide/glycolide to about 85:15 lactide/glycolide. The preferred polymers also have molecular weights in the range of about 50,000 to about 150,000 daltons, preferably about 100,000 daltons.

Lobeline is loaded into the polymer in an amount which allows sustained release of the lobeline from the polymer at the desired therapeutic levels. The preferred loading of lobeline into a PLGA polymer having a lactide/glycolide content of about 85:15 and a molecular weight of about 100,000 daltons, is about 20 to about 65%, more preferably about 30 to about 50%, most preferably about 30 to about 40% by weight of lobeline based on the weight of the polymer.

The formulation of the biodegradable polymer and lobeline, should be such that it permits subcutaneous or intramuscular deposition. These include injectable formulations such as microparticles, microcapsules or elongated rods of the polymer/lobeline composition.

Figure 1A:
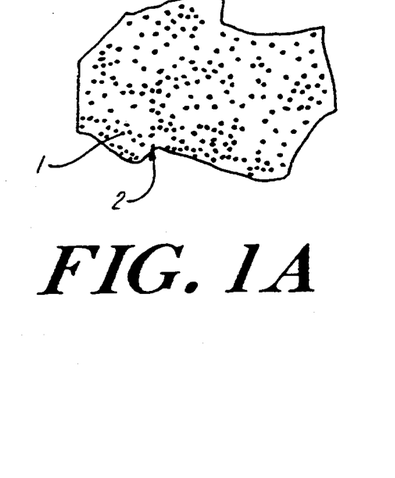
FIGS. 1A, 1B and 1C depict a lobeline containing microparticle, microcapsule and elongated rod, respectively.
Figure 1B:
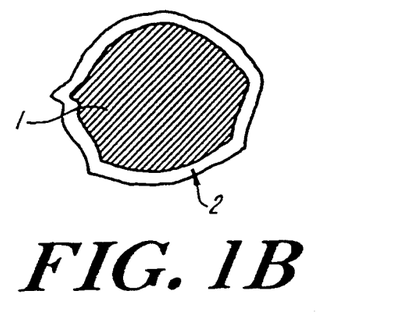
Figure 1C:
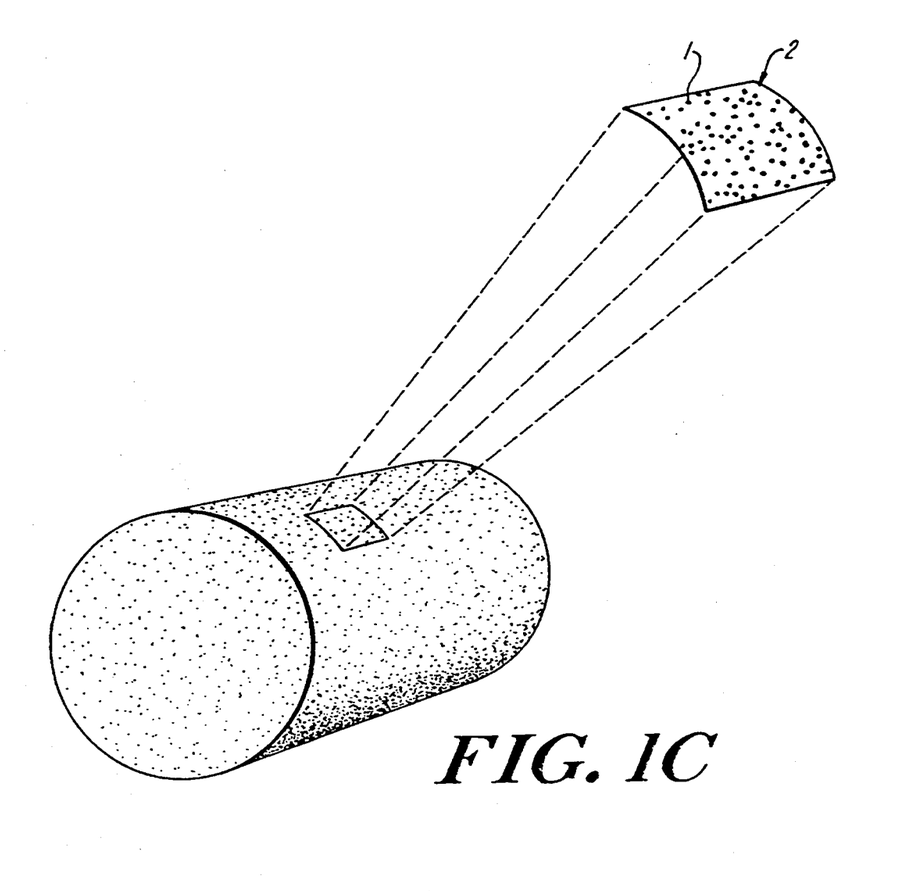

FIGS. 1A–1C depict a lobeline containing microparticle, microcapsule and elongated rod respectively. The lobeline may be distributed throughout the biodegradable polymer 2 as shown in FIGS. 1A and 1C. Alternatively, the lobeline 1 may be encapsulated within the biodegradable polymer 2 as shown in FIG. 1B.

The microparticles, microcapsules, and elongated rods of the biodegradable polymer are of a size capable of being subcutaneously or intramuscular injected or implanted while releasing the lobeline, in a controlled, sustained release manner. Examples of sizes for microparticles include in the range from about 38 to about 250 microns, most preferably 38 to about 106 microns. Examples of sizes for microcapsules include in the range from about 10 to about 250 microns. Examples of sizes for elongated rods include a diameter in the range of about 1 to 4 mm and a length in the range of about 0.5 to about 3 cm.

The preferred form of the biodegradable polymer is microparticles. The microparticles preferably are suspended in a pharmaceutically acceptable vehicle just prior to the time of injection. The pharmaceutically acceptable vehicle is selected such that it can form a suspension with and permit delivery of the microparticles and such that it does not have a significant adverse effect on lobeline's ability to substitute for nicotine when administered in vivo.

Examples of pharmaceutically acceptable vehicles useful for lobeline delivery, include, for example, solutions prepared as follows: Formulation No. 1–0.38 g carboxymethylcellulose, 3.75 g mannitol, and 0.08 g Tween 80 in 20 ml. of distilled water; Formulation No. 2 (preferred)–0.0127 g carboxymethylcellulose, 0.056 g mannitol, 0.027 g Tween 80 in 20 ml. of distilled water. A syringe containing the microparticles can be used to draw up the pharmaceutically acceptable vehicle creating the suspension. Other methods of preparing the suspension of course may be used. The suspension may be created outside of the syringe and then drawn into the syringe. The suspension is injected into the individual preferably at time periods easily integrated with behavioral modification support programs, such as smoking cessation programs.

With respect to lobeline-containing microparticles, it should be understood that the microparticles cannot be suspended in the vehicle for a prolonged period of time because significant amounts of the lobeline would be released from the microparticles into the vehicle. Preferably the suspension is injected within about an hour after being prepared.

When using microparticles (or other forms wherein the amount of drug released will gradually diminish over time), specific dosing procedures may be desirable. For example, if at least 15 mg of lobeline per day were the desired level of sustained release, a dose of microparticles might be prepared to deliver 20 mg per day on day one, with release diminishing to 14 mg per day on day eight. As will be readily understood, the second dose would need to be smaller than the first dose to attain a level of 15 mg per day for the next seven days due to the continued release of lobeline from the residual microparticles of the first dose. Thus, certain PCMS delivery systems will require different dosing schemes.

However, such tapering off of subsequent dose concentrations is unnecessary for lobeline, which is believed to be non-addictive and rapidly cleared from the circulatory system. It is believed that such rapid clearance is due to the binding of lobeline to nicotine receptors located in the brain. Thus, although lobeline may be rapidly cleared from the circulatory system, it may persist in the brain for a substantially longer period of time.

The PCMS also may be part of a transdermal patch. Transdermal patches have a variety of advantages including avoidance of the gastro-intestinal tract, sustained action which readily can be adjusted, self-administration and the ability to immediately discontinue dosage. The term transdermal patch is intended to include patches capable of being affixed to the skin of an individual and having a part or component capable of delivering lobeline, in a controlled sustained release manner. Examples of types of patches useful in this invention include those having a diffusion layer matrix and/or multicompartmental type patches. These will be described in detail below.

There are many transdermal patches known to those of ordinary skill in the art and well described in the prior art. One such patch useful according to the invention is shown generally in FIG. 2. The patch of FIG. 2 involves a diffusion matrix layer that uses a reticulated macroporous polymeric foam as a framework for holding a viscoelastic lobeline-polymer mixture. The patch 10 is a 4-layer, laminated composite that is adapted to be adhered to the skin. The outermost layer, backing layer 12, functions as the primary structural element of the device as well as serving as a protective covering to prevent the lobeline from being transmitted from the device via the outermost surface. Backing layer 12 preferably is made of a sheet or film of a resilient elastomer of about 10–75 microns thick. Examples of such elastomers include polyether block amide copolymers, polyethylene methacrylate block copolymers, polyurethanes, silicon elastomers and the like.

Figure 2:
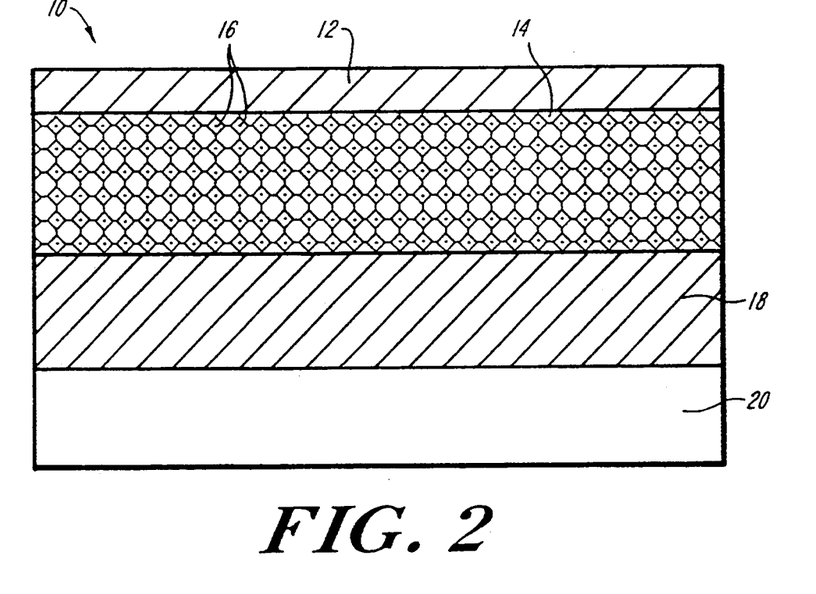
FIG. 2 depicts a transdermal patch having a diffusion layer matrix.

The lobeline-containing matrix layer 14 functions as a reservoir for lobeline, an enhancer, and optionally a pressure sensitive adhesive. The framework of the matrix is a reticulated macroporous polymeric foam 16. Preferably the network is essentially completely open pores (90% or greater). The pore rating of the reticulated foam will normally be in the range of about 10–40 pores per linear centimeter and the density (unfilled) will typically be in the range of about 0.01 to 0.5 g/cm3. Suitable polymers from which such foam frameworks may be manufactured include polyurethanes and polyethylenes.

A pressure sensitive adhesive layer 18 covers the exposed face of the matrix layer 14 and a release liner 20 covers the pressure sensitive adhesive. The pressure sensitive adhesive layer 14 is a medical grade adhesive composition having a thickness normally between about 25 and 100 microns. An example of such an adhesive is polydimethylsiloxane (Dow Corning 355 medical grade adhesive).

The pores of the foam are wholly or partly filled with a viscoelastic hydrophobic lobeline-permeable polymer and an enhancer. The polymer acts as a carrier for the lobeline and the enhancer acts to control the solubility of the lobeline in the polymer and/or absorption of the drug into the skin. The hydrophobic polymer renders the device water-resistant and prevents liquid water from being absorbed by the device, thereby increasing its functionality and wearability. Examples of such polymers are polysiloxanes (silicone polymers), hydrophobic polyacrylates, polyurethanes, plasticized ethylene-vinyl acetate copolymers and the like. An example of a useful enhancer includes Azone ™. The mixture including the lobelike optionally includes an anti-pruritic agent.

Devices of the foregoing nature are generally described in U.S. Pat. No. 4,911,916, entitled "Diffusion Matrix for Transdermal Drug Administration and Transdermal Drug Delivery Devices Including Same", issued Mar. 27, 1990, the entire disclosure of which is incorporated herein by reference. Such patches may be configured to contain sufficient lobeline to release from about five to about thirty milligrams of lobeline per day. Preferably such patches are configured to hold sufficient lobeline to release from about five to about thirty milligrams per day for seven days, such that a single patch may be worn for one week.

The optimum dose range, i.e., the range of doses within which lobeline exhibits maximum therapeutic effect and minimum adverse side effects is determined empirically. The patch or other delivery system is configured and formulated to contain sufficient lobeline to release a dose within the optimum dose range for the desired period of time.

Figure 3:
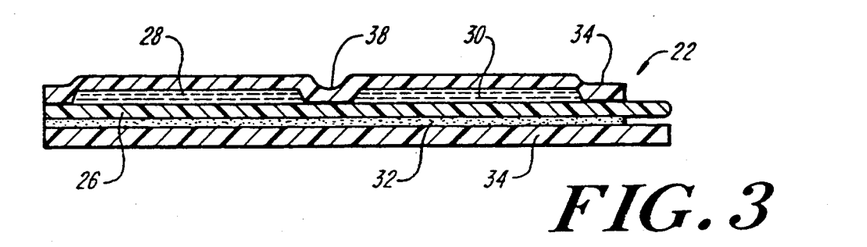
FIG. 3 depicts a multicompartmental transdermal patch.

Another patch useful according to the invention is shown generally in FIG. 3. The patch of FIG. 3 also is a 4-layer composite defining at least two separate compartments. One compartment contains lobeline, and the other compartment contains a delivery substance that when mixed with lobeline permits the delivery of the lobeline transdermally. The patch 22 has a backing layer 24 sealed to a rate controlling membrane 26 in a manner to create two chambers, lobeline containing chamber 28 and a delivery substance containing chamber 30. An adhesive layer 32 covers the rate controlling membrane and a release sheet 34 covers the adhesive layer.

To form the device, a silanized polyester (or other suitable material treated with a releasing agent) approximately 75 microns thick, is used as a release sheet 34. The adhesive layer 32 is cast onto the release sheet, and may be for example polyisobutylene. The adhesive layer then is laminated to the rate controlling membrane 26, which may be about 100 microns thick. Ethylene-vinyl acetate may be employed for the control membrane.

Next, the materials which will become the contents of the lobeline containing chamber 28 and delivery substance chamber 30 are placed in separate areas on the rate controlling membrane 26. The material for the lobeline containing chamber 28 may be lobeline freebase and the material for the delivery substance containing chamber may be an alcoholic or aqueous/alcoholic solution.

Finally, a suitable backing 24 having a heat sealable coating on one surface is placed over the two areas which are to become chambers 28 and 30, and the device is heat sealed 36 around the perimeter and between the two areas to form the two chambers, 28 and 30. The heat seal 38 between the two chambers should be less secure than the heat seal 36 about the perimeter, so that the seal between the chambers will selectively burst under pressure applied by the user. In this manner, pressure may be applied to either one of the chambers to burst the seal between the chambers, thereby mixing the solution and the lobeline and dissolving the lobeline. The lobeline then is in a form which is capable of passing through the rate controlling membrane 26 for delivery to the skin of the user. As with the patch of FIG. 2, the chambers may include enhancers for affecting uptake of the lobeline across the skin.

Preferred forms of the foregoing patch are shown in greater detail in U.S. Pat. No. 4,917,676, issued Apr. 17, 1990 and entitled "User-Activated Transdermal Therapeutic System", the entire disclosure of which is incorporated herein by reference. Such patches should contain sufficient lobeline to release from about five to about thirty milligrams of lobeline per day, and such patches are suitable to provide individual, daily patches.

This invention also pertains to kits useful in aiding an individual in the cessation of smoking. The kits contain a PCMS delivery system according to the invention, as well as instructions for use. For example, a kit for treating nicotine dependence may contain at least one packaged transdermal patch 30 containing the lobeline along with instructions 32 providing information to the user and/or health care provider regarding the use of the patch. The number of transdermal patches provided in the kit may depend on the type of transdermal patch and the length of the smoking cessation program for which the kit is being designed, e.g. a three week or a four week smoking cessation program. In general, the course of treatment is between four and eight weeks, with a six to eight week program being fairly typical.

Figure 4:
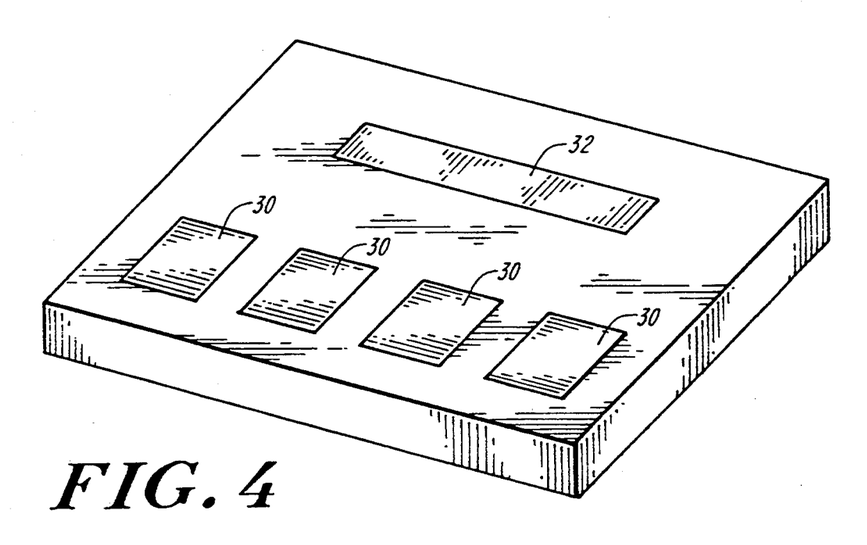
FIG. 4 depicts a kit containing four packaged transdermal patches having a diffusion layer matrix along with instructions.

A transdermal patch containing the lobeline in a diffusion layer matrix typically is designed for long term drug delivery, e.g. about seven days. A kit for a four week smoking cessation program thus may contain four such packaged transdermal patches 30 as shown in FIG. 4. The instructions 32 would inform the individual and/or health care provider to replace the patches on a weekly basis, e.g. Day 1—patch no. 1, Day 8—patch no. 2, etc.

Figure 5:
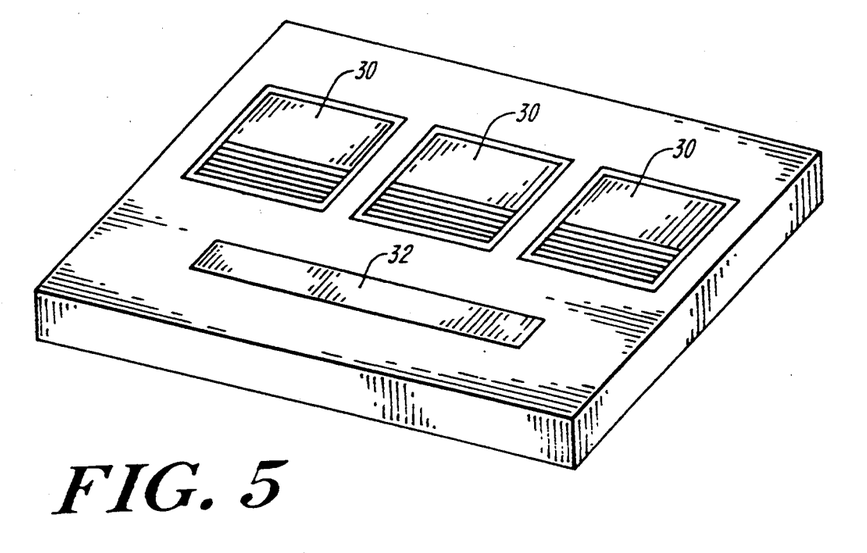
FIG. 5 depicts a kit containing twenty-eight packaged multicompartmental transdermal patches along with instructions.

A multicompartmental transdermal patch typically is designed for daily use. A kit for accompanying a three or four week smoking cessation program may contain twenty-one or twenty-eight, respectively, multicompartmental transdermal patches 30 as shown in FIG. 5. The instructions 32 would inform an individual and/or health care provider to replace the transdermal patch on a daily basis and also would instruct the individual how to contact the lobeline in the first compartment with the delivery substance in the second compartment. For example, the individual may have to break a pressure sensitive seal between the two compartments.

Figure 6:
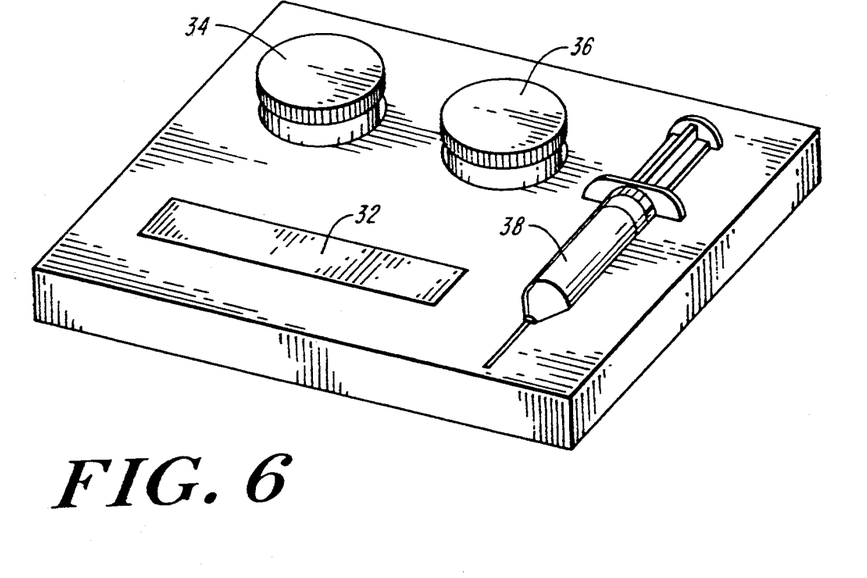
FIG. 6 depicts a kit including a syringe containing microparticles of a biodegradable polymer containing lobeline, a container of a pharmaceutically acceptable vehicle, and instructions.

The kit also may include at least one container 34 of an injectable or implantable PCMS delivery system and instructions 32 for use as shown in FIG. 6. For example, the kit may include four to eight containers of polymer/lobeline microparticles useful for a four to six week smoking cessation program. As discussed above, each container may need to contain a different amount of microparticles/lobeline to account for continued release of the lobeline from microparticles remaining from each earlier dose. Alternatively, each container may contain the same quantity of microparticles/lobeline with instructions to inject a reduced volume of resuspended microparticles/lobeline on subsequent days of the treatment period. However, as noted above, it may not be necessary to decrease the dose level during the treatment program for lobeline because lobeline is believed to be non-addictive and rapidly cleared from the circulatory system.

The kit may further include at least one container 36 of a pharmaceutically acceptable vehicle. A syringe 38 also may be provided in the kit. The syringe may be pre-loaded with microparticles.

The following non-limiting examples further illustrate the present invention.

EXAMPLE 1—Preparation of PLGA Microparticles Containing 30% Lobeline

Lobeline free base was obtained from Sigma Chemical company or prepared from lobeline sulfate obtained from Boehringer Ingelheim. The compound was characterized prior to use by UV spectroscopy, HPLC, and melting point. MEDISORB ™ 8515DL lactide/glycolide bioresorbable polymer was obtained from DuPont. By specification the polymer is 85±5% lactide and 15±5% glycolide. The solvents (highest grade available) were obtained from Fisher Scientific. The polymer (3.5044 g) was dissolved in methylene chloride (23 ml.) as a 15% solution by weight. Lobeline (1.5006 g) was added to the polymer solution and the solution was stirred to insure complete mixing. The solution was then cast onto a clean, level piece of plate glass and spread with a Boston-Bradley adjustable blade. After evaporation of most of the solvent under a nitrogen stream, the film was peeled from the glass and vacuum desiccated.

The film formed in the casting step was of very low density because the solvent removal step left a very large void volume. The void volume was reduced to decrease permeation of fluids into the microparticles by a compression step, utilizing heat and hydraulic pressure. The film was extruded into rods with a Pasadena Hydraulic Press at about 70° C.

The extruded rods were ground into small particles using a commercial grinder with a cooled grinding chamber. Following grinding, the powder or small particles were passed through USP sieves to collect microparticles in the size ranges of about 38 to 106$\mu$, 106-150$\mu$ and 150-180$\mu$. The microparticles containing 30% lobeline were collected.

EXAMPLE 2—Preparation of PLGA Microparticles containing 40% Lobeline

Example 1 was repeated except 1.0000 g of lobeline was placed in the jar with the polymer solution (1.501 g in 10 ml.). The microparticles containing 40% lobeline were formed and collected.

EXAMPLE 3—Preparation of PLGA Microparticles containing 50% Lobeline

Example 1 was repeated except 2.0016 g of lobeline was placed in the jar with the polymer solution (2.0016 g in 13 ml.). The microparticles containing 50% lobeline were formed and collected.

EXAMPLE 4—The In vitro Release of Lobeline from PLGA

Figure 7:
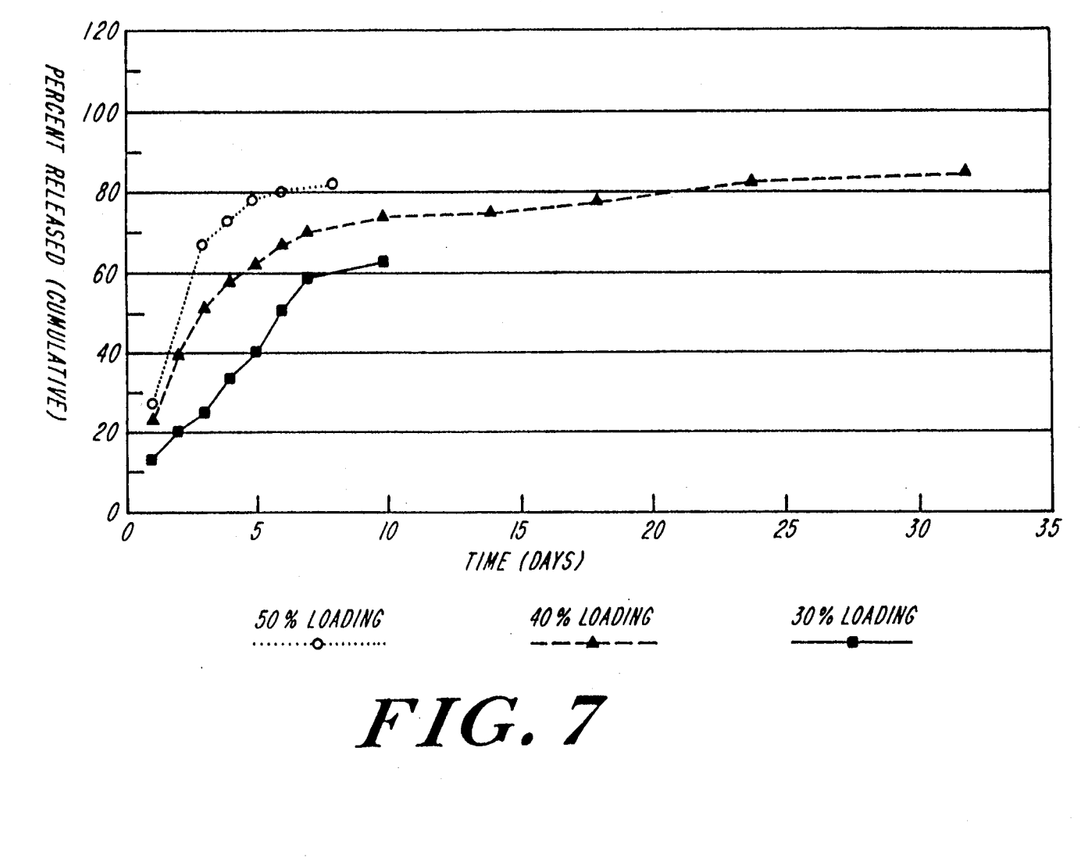
FIG. 7 depicts the in vitro release of lobeline free base from PLGA microparticles (150–180$\mu$) at 30%, 40%, and 50% lobeline loading.

The PLGA/lobeline microparticles prepared in Examples 1, 2, and 3 were exposed to a phosphate buffered saline (PBS) solution under simulated sink conditions such that the drug would never reach more than 20% concentration in the buffer. The microparticles were placed in a thimble which was further placed in a test tube. Each day the thimble was moved to a new test tube and the lobeline content in the PBS solution was measured by extraction and concentration in an organic solvent, followed by UV analysis. Analysis of the buffer for lobeline content was made on a daily basis in the first two to three days, then on a weekly schedule thereafter. The results are depicted in FIG. 7. FIG. 7 depicts the release of lobeline free base from PLGA microparticles (150-180$\mu$) at 30%, 40%, and 50% lobeline loading.

In none of the systems was the entire lobeline content released within one week. The 30% loading exhibited the slowest release. In the 30% loading, for the 150-180$\mu$ particles, only 60% of the lobeline was released at the end of the first week.

EXAMPLE 5—The In vitro Release of Lobeline from PLGA

The method of analysis for this example differs from example 5 above in that the amount of lobeline left in the microparticles was measured after leaching the microparticles in the PBS solution. The total amount left in the microparticles was subtracted from the amount initially loaded into the microparticles to obtain the amount released.

Figure 8:
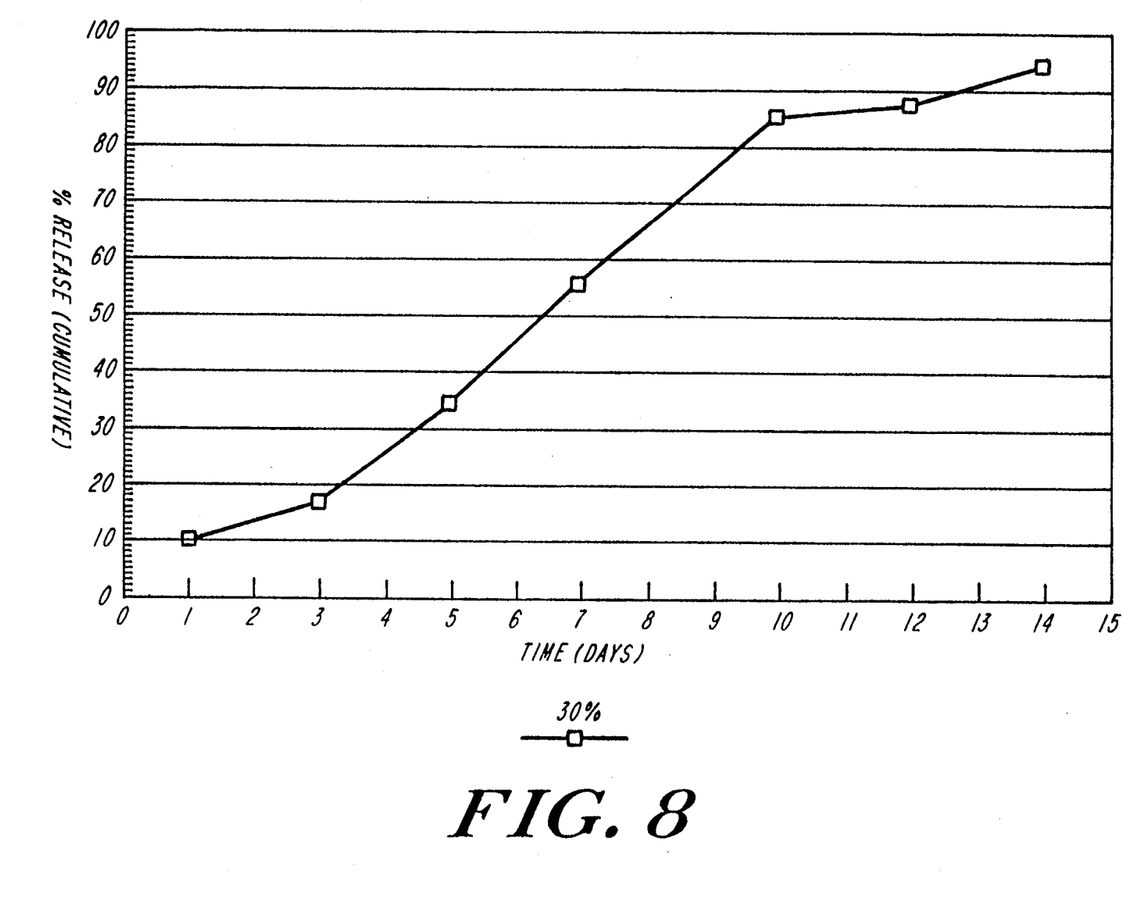
FIG. 8 depicts the in vitro release of lobeline free base from PLGA microparticles (38–106$\mu$) at 30% lobeline loading.

The particles themselves differed as well, in that 38-106$\mu$ sized microparticle, prepared as described in Example 1, were used. The microparticles were placed in an extraction thimble and covered with a glass wool plug. The thimbles were suspended in phosphate buffered saline containing 0.1% sodium azide. (9 thimbles/1.7 L). Each day the samples were removed, air dried, then vacuum dried. Each dry thimble was transferred to a large test tube and enough $CH_2Cl_2$ was added to cover the thimble. The tube was vortexed to aid in dissolving the microparticle. To each tube, a measured volume of 0.01N $H_2SO_4$ was added. After mixing, the acid layer was removed and the step was repeated two to three times. The acid fractions were analyzed by UV for lobeline content. The total amount found was subtracted from the initial value to obtain the amount of lobeline released from the microparticles. The results are depicted in FIG. 7. FIG. 8 depicts the release of lobeline free base from PLGA microparticles (38-106$\mu$) at 30% lobeline loading. The release was substantially constant over the first 10 days, tapering off over the last 4 days.

EXAMPLE 6—Materials and Methods—Release Study of Two formulations in Rats

Formulations

Two formulations were tested. One formulation contained PLGA microparticles at 30% lobeline free base loading, and the other formulation contained PLGA microparticles at 40% lobeline free base loading. Within ½ hour of injection, a suspension containing 20 mg/ml of 30% formulation or 15 mg/ml of 40% formulation was prepared in diluent (0.94 g carboxymethylcellulose, 9.38 g of D-Mannitol, 0.2 g polysorbate 80 (Tween 80) in 50 ml of water).

Animal Tests

Female Sprague-Dawley Rats (250-300 g) were used. Two animals were used as negative controls. An aliquot of 0.1 ml of vehicle was injected into the scapular region of each animal from a syringe fitted with a 22 gauge needle. On day 7, the two animals were sacrificed with $CO_2$ and the fatty tissue in the scapular region was removed.

The remaining animals were divided into two groups: those receiving the 30% formulation and those receiving the 40% formulation. From each group, four animals were used as positive controls. These animals were sacrificed and the fatty tissue and facia in the scapular region was removed. Prior to the time of analysis, an aliquot of 0.1 ml of the formulation in vehicle was added to the tissue sample.

From each group, five additional subgroups were selected, representing different periods of time that the suspensions were left in the animal prior to obtaining a tissue sample: 4 hrs; 1 day; 2 days; 5 days; and 7 days. There were four animals in each of these subgroups.

The formulations were prepared for use as described above, and in every case a 0.1 ml aliquot was given. At the time of sacrifice, the fatty tissue and facia in the scapular region of each animal was removed. In most, but not all cases, areas of tissue containing microparticles could be observed. It seems likely, however, that some of the microparticles migrated to areas beyond the excision site and that this material was thus not recovered.

Tissue Extraction

A tissue sample along with 2-3 ml $CH_2Cl_2$ was placed in a short glass test tube. 100 ul of a 1 mg/ml solution of triprolidine in $CH_2Cl_2$ (internal standard) was added. Using the Tissue Tearor ™ at 4500-8000 rpm, the sample was homogenized. The sample was transferred to a centrifuge tube with a teflon-lined screw cap and centrifuged for 7 min. The $CH_2Cl_2$ was carefully pipetted out and transferred to a test tube. To this solution 1 ml of 0.01N $H_2SO_4$ was added and the mixture was vortexed for 15-20 seconds. After separation of phases had occurred, the top (acid) layer was carefully removed with a pipette and the volume of this acid solution was measured. The acid solution was then transferred to a new, clean test tube or vial and filtered through 0.45u nylon filter prior to injection. The extraction of the $CH_2Cl_2$ with acid was repeated until no more lobeline was detected or a maximum of five repeats.

Analysis

The acid samples were analyzed directly by HPLC. The amount of lobeline recovered was based on a standard curve of extracted lobeline concentration/internal standard concentration from spiked tissue control samples at various lobeline levels.

The HPLC System used was as follows: Waters 510 pump; Waters U6, injector; Waters Lambda Max 481 LC Spectrophotometer; spectra Physics SP 4270 Integrator; Phenomenex Partisil $C_8$ 5u 100×4.6 mm column with 30×4.6 mm guard column with same packing.

The mobile Phase was: 60% Phosphate Buffer, pH 3:40% (50:50 $CH_3CN$/MeOH). The flow rate was 1.2 ml/min; AUFS 1.0; detection at 249 mn; with 4 ul sample injection volume.

The results for 30% and 40% loaded microparticles were adjusted for an efficiency of extraction from excised tissue of 75.4%. No adjustment has been made for efficiency of recovery of microparticles from the animals.

Figure 9:
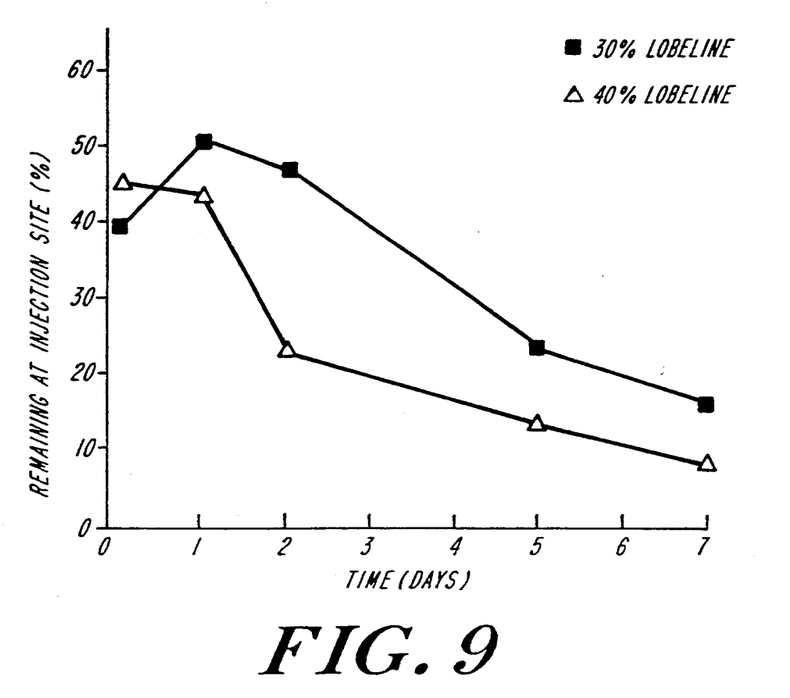
FIG. 9 depicts the in vivo release of lobeline free base, expressed as the percentage of lobeline remaining at the injection site, from a formulation containing 30% lobeline free base and a formulation containing 40% lobeline free base.

The results (shown in FIG. 9) are presented graphically, with the percent of the dose found in the tissue sample plotted against different kinds of treatment duration. The 30% loading exhibited a somewhat more linear release profile than the 40% loading.

EXAMPLE 7—Evaluation of Polyethylene "Pouches" for in vivo Release Studies in Rats Formulation The method of analysis for this example differs from example 6 above in that a single formulation containing PLGA microparticles at 35% lobeline free base loading was tested. The formulation was sealed into polyethylene bags with 20μ pores prior to implantation in the scapular region of rats. These bags are porous enough for use in dissolution studies, yet have pores small enough to retain the microparticles (smallest particle diameter is 38μ).

Method

Polyethylene pouches (Biotek, Woburn, Mass.) were used. Twelve pouches were heat sealed without filling and cut to a size of about 1 cm×1 cm. The remaining pouches were each filled with approximately 4 mg of the above formulation and similarly sealed and trimmed. Female Sprague Dawley rats of approximately 250 g each were obtained and quarantined. At time zero (T=0), each rat was anesthetized and an incision just larger than the width of the pouch was made in the scapular area. The pouch was held with forceps and dipped into normal saline, then the forceps were used to slip the pouch under the skin. The incision was closed with one or two staples. On days 1, 2, 3 and 7, the pouches were removed from six controls (empty pouches) and six animals (for each time point) which had received the formulation. The method of removal was to anesthetize the animal and then to make an "L" shaped incision around the site of the pouch. The pouch was exposed by lifting the skin. Each pouch was rinsed in a normal saline solution and patted dry on a paper towel. The pouches were stored in sealed polyethylene bags overnight in the freezer and analyzed the next day. All animals were sacrificed immediately following removal of the pouches.

Sample Preparation for HPLC Analysis

Each pouch was cut open and its contents, along with the emptied, shredded pouch, were added to a 10 ml volumetric flask containing approximately 5 ml of acetonitrile. The flask was sonicated for 10 minutes, allowed to cool to room temperature (approximately 30 minutes) and the total volume in the flask was brought to 10 ml (i.e., "Q.S. to volume") with acetonitrile to prepare a "stock solution". Thereafter, 0.1 ml of the stock solution was accurately transferred to a 10 ml volumetric flask and Q.S. to volume with working diluent (described below). A 2.5 ml aliquot of this solution was then transferred to another 10 ml volumetric flask and Q.S. to volume with working diluent.

HPLC Analysis

The acid samples were analyzed directly by HPLC. The amount of lobeline released from each pouch was based on a standard curve of lobeline concentration/internal standard concentration at various lobeline levels. HPLC analysis was performed as described above, with the following modifications.

Internal Standard Preparation: Triprolidine (10.0 mg) was accurately weighed and quantitatively transferred to a 10 ml type A volumetric flask and Q.S. to volume with mobile phase to give an Internal Standard Stock Solution having a Triprolidine concentration of 1.0 mg/ml. This stock solution was used to prepare the Working Diluent.

Working Diluent: A type A volumetric pipette was used to accurately transfer 1 ml of the Internal Standard Stock Solution to a 100 ml volumetric flask and Q.S. to volume with mobile phase (described below). Thereafter, 5 ml of the latter solution was accurately transferred (type A volumetric pipette) to a second 100 ml volumetric flask and Q.S. to volume with mobile phase to prepare the Working Diluent. The Working Diluent had a Triprolidine concentration of 500 ng/ml.

Standard Preparation: Lobeline reference standard (10.0 mg) was accurately weighed and quantitatively transferred to a 10 ml type A volumetric flask and Q.S. to volume with mobile phase to provide a Lobeline Stock Solution having a lobeline concentration of 1.0 mg/ml. A type A volumetric pipette was used to accurately transfer 1 ml of the Lobeline Stock Solution to a 10 ml volumetric flask and Q.S. to volume with Working Diluent. Thereafter, 1 ml of the latter solution was accurately transferred (type A volumetric pipette) to a second 10 ml volumetric flask and Q.S. to volume with Working Diluent to prepare the Standard Lobeline Solution. The Standard Lobeline Solution had a lobeline concentration of 0.01 mg/ml.

Mobile Phase: All solutions were degassed and filtered through a 0.2 micron membrane filter before use.

The mobile phase was prepared by adding 200 μl triethylamine to one liter of a mixture containing 62% 40 mM phosphoric acid (pH 3.00) and 38% acetonitrile.

Operating Conditions: The Column was Phenomenex/Partisil 5C8 (25.0 cm×4.6 mm i.d.). The flow rate was 1.0 ml/min; detection was at 249 nm; with a 35 μl injection volume.

Figure 12:
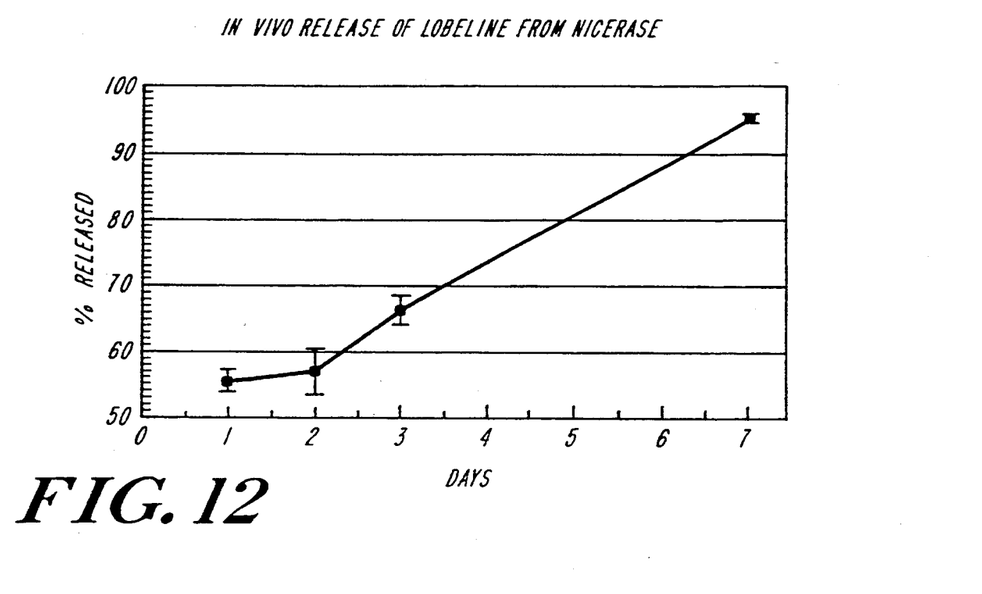
FIG. 12 depicts the in vivo release of lobeline free base, from PLGA microparticles at 35% lobeline loading.

The results (shown in FIG. 12) are presented graphically, with the average percent of lobeline released from the six pouches plotted as a function of treatment duration. The time points set forth in the figure represent the average of six replicates. At the end of one week, the percent lobeline released from the pouch in the test samples was approximately 95%. The results indicate that substantially all of the lobeline contained in the microparticles is released by day seven.

EXAMPLE 8—Materials and Methods—Efficacy Study of Lobeline Sulfate in Humans

Test Subjects

The test subjects consisted of long-term or chronic smokers who were smoking regularly for more than five years. They were smoking habitually 20 or more cigarettes per day. All volunteers were healthy, non-obese, male adults without history of gastrointestinal, hepatic, neurological or hematological abnormalities. Prior to enrollment for the study, each volunteer was examined for normalcy.

Method

On days 1, 2, 3, and 4 of the drug administration test, a quantity of 0.4, 0.6, 0.8 or 1 ml of 20 mg/ml lobeline sulfate solution was injected subcutaneously on the upper ⅓ of ventral aspect of the forearm. The volunteers were then free to smoke as per their desire and report on the number of cigarettes smoked and puffs taken for 2 hours after the injection.

Results

Figure 10:
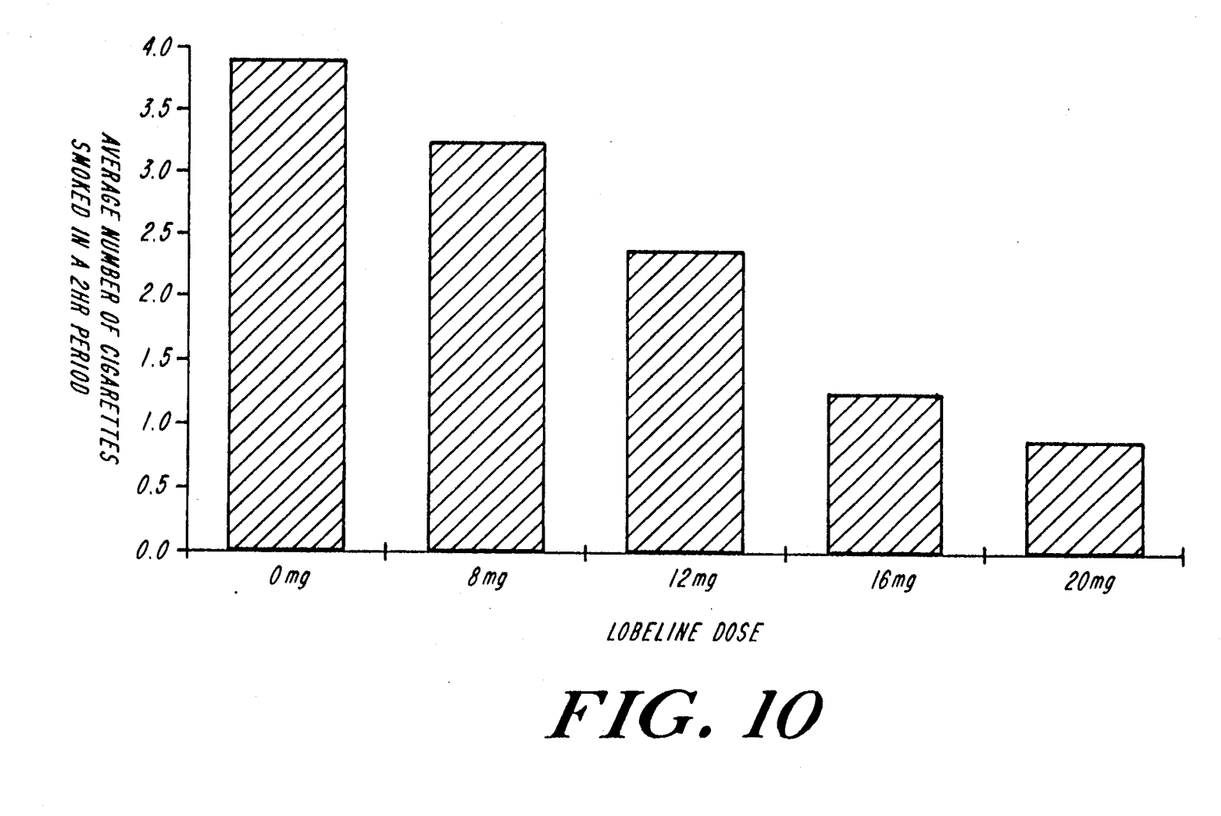
FIG. 10 depicts the in vivo effect of lobeline dose on the number of cigarettes smoked.
Figure 11:
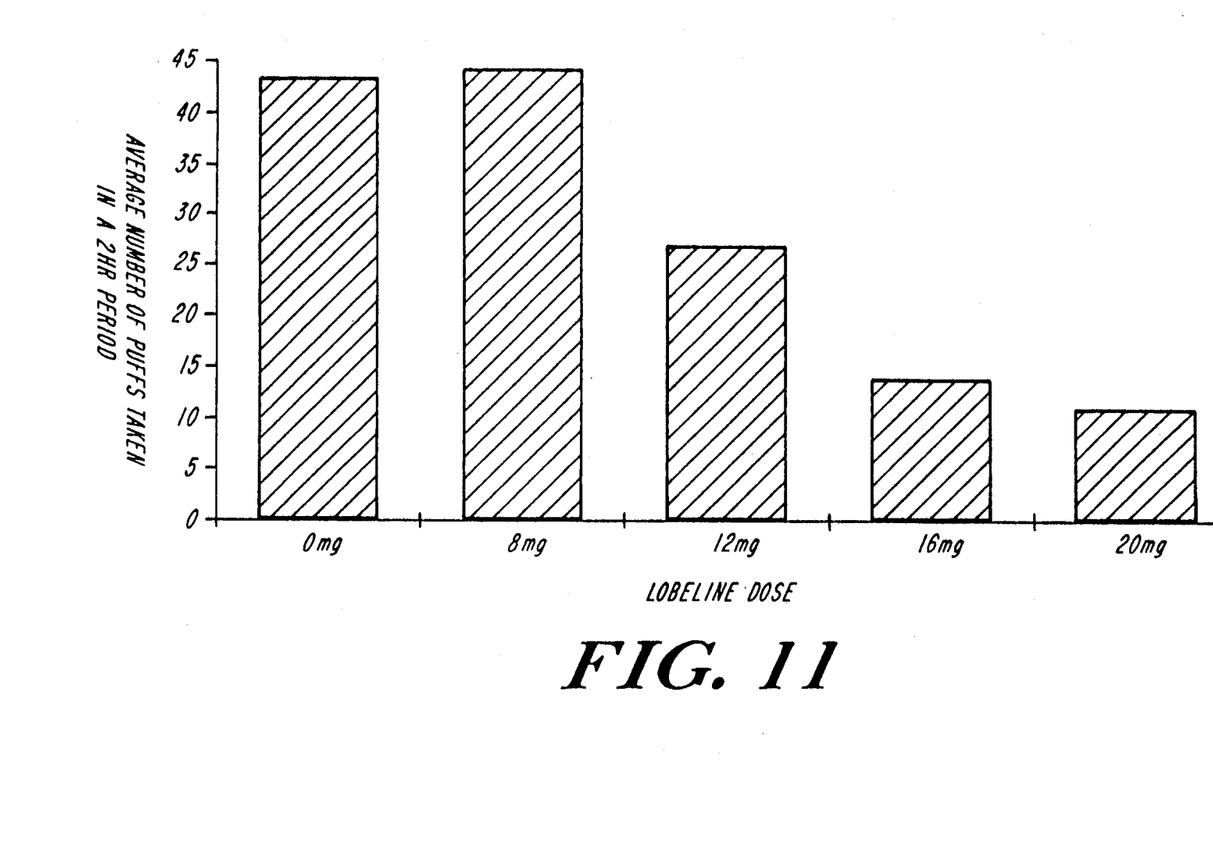
FIG. 11 depicts the in vivo effect of lobeline dose on the number of smoking puffs.

Both the number of cigarettes smoked and the number of puffs taken in the period of 2 hours after lobeline injection decreased as the dose given increased. The results are illustrated in FIGS. 10 and 11. As shown in FIG. 10, the average number of cigarettes smoked in a two hour period immediately following treatment with lobeline sulfate decreased substantially linearly as a function of the lobeline dose. Similarly, the average number of puffs taken in a two hour period immediately after treatment with lobeline sulfate decreased markedly as lobeline increased, although the initial effects were not observed until a dose of at least 12 milligrams was administered.

EXAMPLE 9—Materials and Methods—Efficacy Study of Lobeline-Containing Microparticles in Humans

Test Subjects

A total of twelve volunteers (9 test subjects and 3 placebo subjects) were selected according to the criteria described above in Example 8. With the exception of two volunteers who smoked 7 and 10 cigarettes per day, the remaining volunteers smoked, on average, approximately 20 cigarettes per day.

Formulation

A formulation comprising PLGA microparticles containing lobeline was prepared according to the method described in Example 1. However, the concentration of lobeline was adjusted to provide microparticles containing 35% lobeline by weight. Prior to injection, the formulation was resuspended in a diluent (D-mannitol (50 mg), carboxymethyl cellulose sodium (5 mg), polysorbate-80 (1 mg) and water for injection Q.S. to 1 ml) to form a homogeneous suspension.

Method

Figure 13:
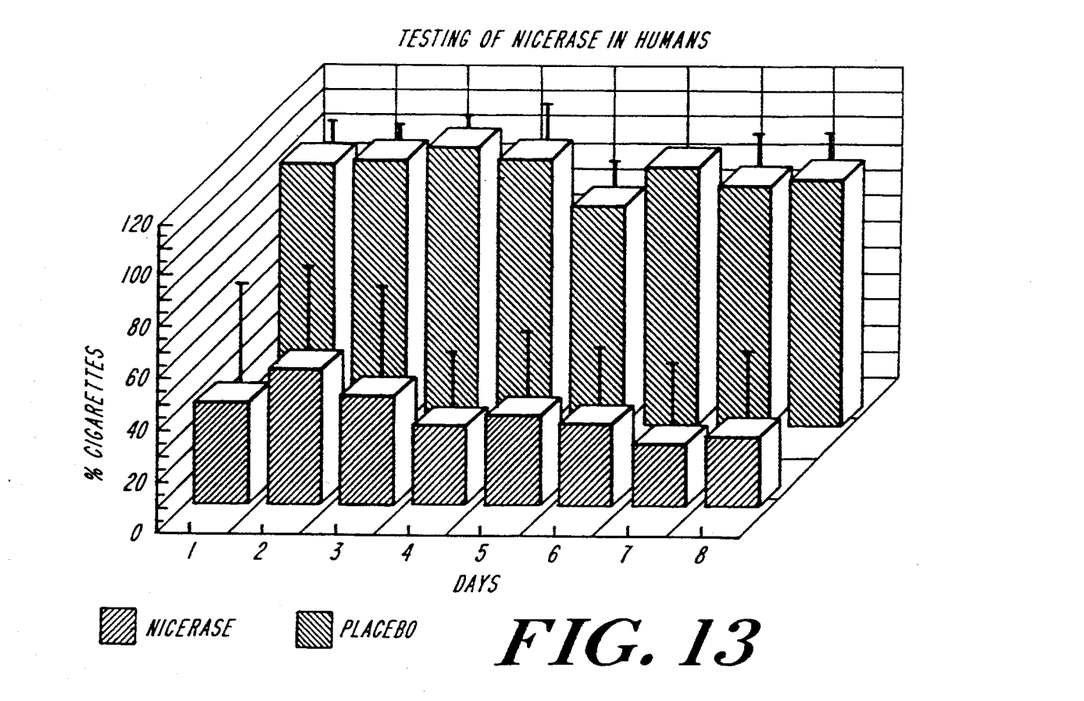
FIG. 13 depicts the in vivo effect of a lobeline-containing microparticle formulation on the number of cigarettes smoked by human volunteers following subcutaneous injection of the microparticles.

On days 1 and/or 2 of the drug administration test, a quantity of between approximately 0.6 ml to 0.8 ml of the above-described lobeline suspension was injected subcutaneously as described in Example 8. The volunteers were then free to smoke as per their desire and report on the number of cigarettes smoked for eight days. These results are shown in FIG. 13, where day 1 represents the first full day following initial injection.

Results

The number of cigarettes smoked in the period following the injections decreased in comparison to the number of cigarettes consumed prior to injection. The results are illustrated in FIG. 13. As shown in FIG. 13, the number of cigarettes smoked in a 24 hour period compared to the number of cigarettes smoked prior to treatment is reported as the % cigarettes smoked. This percentage decreased substantially following injection of the lobeline suspension.

EQUIVALENTS

Those skilled in the art will be able to ascertain, using no more than routine experimentation, many equivalents of the specific embodiments of the invention described herein.

These and all other equivalents are intended to be encompassed by the following claims.

We claim:

1. A method of treating an individual for nicotine dependence comprising:
   administering subcutaneously, intramuscularly or by implantation at least one drug delivery system to an individual, said drug delivery system comprising at least one microparticle having a composition of lobeline in a biodegradable polymer which releases an effective amount of lobeline to diminish the individuals' desire for nicotine for a period of time having a duration of at least one day.

2. The method of claim 1 further comprising administering behavior modification counseling to said individual as part of a smoking cessation program.

3. The method of claim 1 wherein said period of time has a duration of at least one week.

4. The method of claim 1 wherein said biodegradable polymer is selected from the group consisting of poly(lactic/glycolic)acid copolymers, polylactic acid, polyglycolic acid, polyesters, polyorthoesters, polylactones, polyanhydrides, and polyaminoacids.

5. The method of claim 4 wherein said biodegradable polymer is poly(lactic/glycolic) acid polymer.

6. The method of claim 5 wherein said poly(lactic/glycolic) acid polymer is about 50:50 to about 85:15 lactide/glycolide.

7. The method of claim 1 wherein said microparticles are of a size of about 38 to about 250 μm.

8. The method of claim 1 wherein said biodegradable polymer is carried in a pharmaceutically acceptable injection vehicle.

9. The method of claim 8 wherein said pharmaceutically acceptable injection vehicle comprises a solution of carboxymethylcellulose.

10. The method of claim 1 wherein said physical constraint modulation system releases from about 56 to about 114 mg of lobeline over a period of time having a duration of seven days.

* * * * *